United States Patent [19]
Wilkinson

[11] Patent Number: 5,190,048
[45] Date of Patent: Mar. 2, 1993

[54] THERMISTOR AIRFLOW SENSOR ASSEMBLY

[75] Inventor: Mark A. Wilkinson, Marietta, Ga.

[73] Assignee: Healthdyne, Inc., Marietta, Ga.

[21] Appl. No.: 761,293

[22] Filed: Sep. 17, 1991

[51] Int. Cl.⁵ ............................................. A61B 5/087
[52] U.S. Cl. ...................................... 128/724; 128/736
[58] Field of Search ................................ 128/724–725, 128/716, 671, 736, 639–640; 338/22 R; 29/620

[56] References Cited

U.S. PATENT DOCUMENTS

| | | | |
|---|---|---|---|
| 2,943,628 | 7/1960 | Howell | 128/640 |
| 3,232,288 | 2/1966 | Krobath | 128/724 |
| 3,241,549 | 3/1966 | Tyler | 128/724 |
| 3,884,219 | 5/1975 | Richardson et al. | 128/724 |
| 3,935,742 | 2/1976 | Rybak | 73/336.5 |
| 3,946,726 | 3/1976 | Pikul | 128/725 |
| 3,999,537 | 12/1976 | Noiles | 128/724 |
| 4,183,136 | 1/1980 | Colla | 29/620 |
| 4,353,372 | 10/1982 | Ayer | 128/640 |
| 4,777,963 | 10/1988 | McKenna | 128/724 |
| 4,971,065 | 11/1990 | Pearce | 128/721 |
| 5,069,222 | 12/1991 | McDonald, Jr. | 128/724 |

Primary Examiner—Lee S. Cohen
Assistant Examiner—Jeffrey R. Jastrzab
Attorney, Agent, or Firm—Foley & Lardner

[57] ABSTRACT

A thermistor airflow sensor assembly adapted to be mounted adjacent the mouth and nose of a patient for monitoring the breathing of the patient, with the assembly comprising thin, flexible, resilient layers of film adhesively secured to each other to form a laminate. Copper conductor strips are formed by etching away a copper layer attached to the lower film prior to lamination, with chip thermistors being soldered to the copper conducting strips. The thermistors are mounted in leg portions extending laterally from a main body strip of the assembly, with two legs being adapted to be aligned with the nostrils of the patient, and the opposed leg extending downwardly to a position where the outer end thereof is generally aligned with the mouth of the patient. The copper conducting strips extend through an enlarged end portion of the assembly for electrical connection to a cable, a bend relief cable, and a plug which can be connected to a monitor for providing visual and/or audio alarm signals when breathing has been interrupted. A separate carrier strip can be mounted on the film layer adapted to be positioned against the face of the patient, whereby the thin flexible assembly can be easily adapted to the facial configuration of the patient. The entire assembly, including adhesive and the copper conductor strips, is in the range of 0.006″–0.008″ in thickness, except for the thermistor locations and the strain relief area.

10 Claims, 1 Drawing Sheet

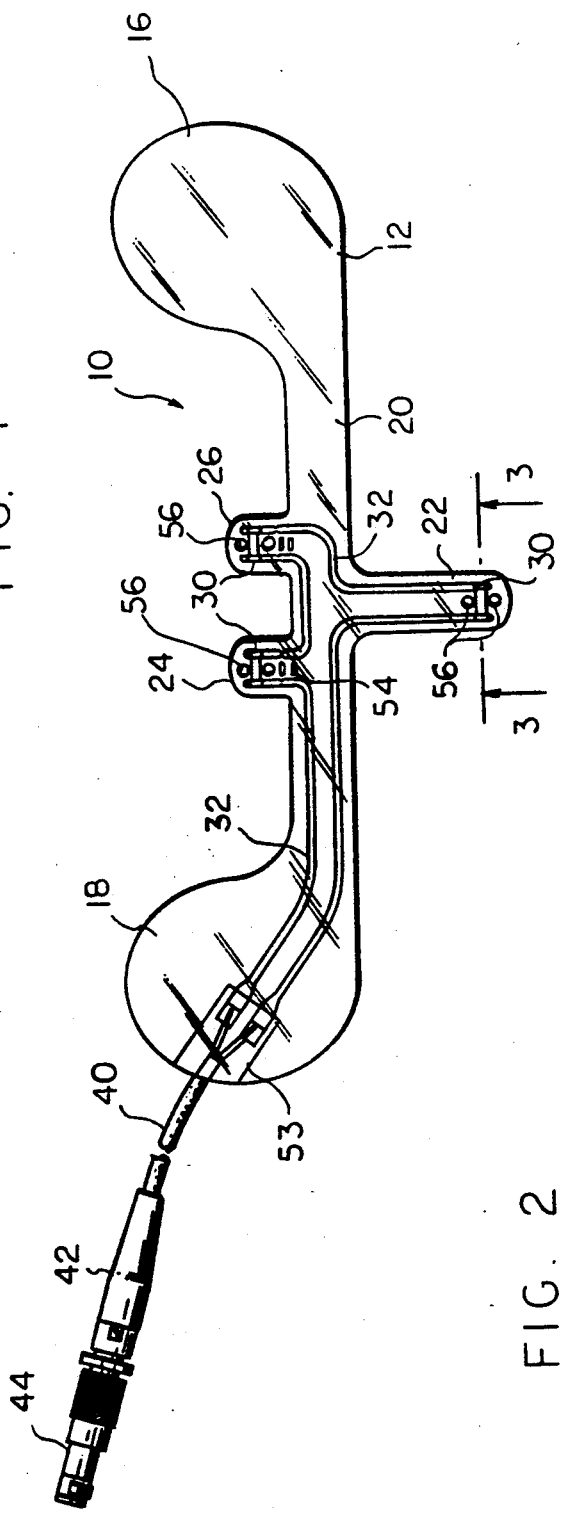
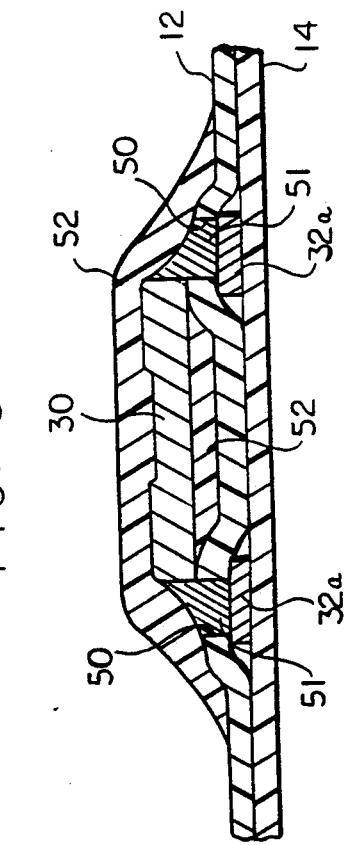

5,190,048

THERMISTOR AIRFLOW SENSOR ASSEMBLY

BACKGROUND OF THE INVENTION

The present invention relates, as indicated, to a thermistor airflow sensor assembly and relates more particularly to a sensor assembly for monitoring the breathing of patients.

Sleep apnea is a term used to refer to a temporary break or suspension in respiration, and frequently occurs in persons of all ages. It is a particularly difficult problem with infants. There are various methods of monitoring sleep apnea, with one of these comprising the monitoring of the breathing cycle. The use of thermistors is widely known for this purpose, with the thermistor sensing quickly and accurately the differences between ambient temperature and the temperature of the expired air, and changing its resistance in response thereto. This change in resistance can be visually displayed.

In thermistor sensor systems, a thermistor is typically placed adjacent each nostril or naris of the nose and also adjacent the mouth so that nasal and oral airflow, respectively, can be monitored. When the patient or user is breathing normally, the monitoring device to which the thermistors are connected will provide a read out indicative of normal breathing. The absence of temperature change is indicative of at least a temporary cessation of expiration of air, and this condition can be quickly read out visually on the monitor as well as actuating an audible alarm. As described, merely the presence or absence of breathing is detected by the monitoring system, although more sophisticated systems can be utilized which additionally monitor the temperature and quantity of air expired, moisture content, etc.

The use of thermistors for the purpose indicated has in the past presented certain problems with respect to the mounting of the thermistors on the user. Typical arrangements still in use at this time comprise the use of thermistor beads attached to wires which must be taped to the face of the user and arranged under the nose and in front of the mouth of the user. This arrangement has obvious disadvantages. The taping is inconvenient, unsightly, and frequently ineffective since the tape can be pulled from the face and the monitoring function thus disrupted. Moreover, a taped mounting of this type is very uncomfortable and lacks durability since the thermistor beads and connecting wires are freely exposed for possible damage.

A proposed solution to the above problem is disclosed in U.S. Pat. No. 4,777,963, in which thermistors adapted to be placed adjacent the naris and mouth are carried by a support member which includes a removable release paper which when stripped away uncovers an adhesive surface for securing the support member to the skin of the patient. The support member includes an upper portion which can be bent to contact the user over the bridge of the nose and the areas on each side thereof. A second, lower portion, carries the thermistors and can be folded upwardly so that such portion is adhesively attached to the face of the wearer below and to either side of the nose, and between the nose and the lips. The oral thermistor extends downwardly from the lower portion so that it can be positioned outwardly of the mouth for receiving orally expired air.

Although the respiration monitor disclosed in U.S. Pat. No. 4,777,963 does solve certain of the earlier problems noted, it too has clear disadvantages. The construction is such that manual assembly of the thermistors and lead wires therefor on the support member is necessary. All thermistors are exposed which, because of their relatively small size and brittle nature, can lead to premature damage. The possibility of thermistor damage is recognized by patentee who provides both a mesh covering and an outer elastic sleeve around the thermistors to guard against potential inhalation of fragments of the thermistors in the event the thermistors are broken. This precautionary measure is time consuming and adds to the cost of the assembly. Further, the ability of the device to firmly seat on the patient varies tremendously with the facial configuration of the patient. This increases the potential for misalignment of the thermistors with the nostrils.

SUMMARY OF THE INVENTION

An object of the invention is to provide a nasal-oral airflow sensor assembly which can be easily applied, is comfortable during use and is very stable once in place. A further object of the invention is to provide an airflow sensor assembly which is comparatively inexpensive to manufacture and which is durable in use. In fact, with the use of a cleaning solution following use, the assembly can be repeatedly re-used without deterioration. This also significantly reduces cost on a per application basis.

The objects of the invention are achieved by the provision of an airflow sensor assembly principally characterized by the mounting of chip thermistors on a flexible printed circuit. The circuit is embedded within a very thin laminated film assembly which comprises the body of the device, with the film laminate being flexible to facilitate mounting the assembly on various facial configurations of users. The shape of the assembly is such that the primary areas of mounting are in the vicinity of the cheek bones of the user thereby providing a relatively large and receptive mounting surface. To facilitate mounting, a separate doublesided foam tape is preferably supplied with the sensor assembly. One side of the foam tape adheres to the surface of the assembly which is to abut the face, with the removal of the other releasable side of the tape permitting the temporary bonding of the assembly to the face of the user.

A further feature of the invention is that the thermistors and conductors and leads therefor are embedded or encapsulated. Very thin, preferably copper conductor strips are used to interconnect the thermistors with a cable which is in turn connected to a plug for connection to monitoring equipment which forms no part of the present invention. The embedding or encapsulation provides not only a safe, electrically isolated circuit, but also substantially increases the durability of the assembly since no electrical components, including the thermistors, are exposed. The copper conductors are etched during the assembling process as will be hereinafter described, and the thermistors, although extending outwardly from the surface of the film layers, are coated with a preferably polyurethane coating which does not detract from thermal conductivity.

The sensor assembly of the present invention is further characterized by its inherent reliability, durability, and comparatively inexpensive manufacture. The assembly components are widely available and relatively inexpensive, and assembling can be effected quickly and easily. The assembly is highly reliable in use and very durable due to the materials used and the isolation of the circuit components.

The assembly comprises a first layer of plastic film on which copper conductors are provided, preferably by etching. A second, identically configured film layer is then adhesively secured to the first by an adhesive film or liquid adhesive, as desired. The top film is not attached at the region where the cable is connected to the copper conductors so as to provide strain relief in the cable connecting area. The film layers are formed with arms which extend transversely to a relatively narrow main body portion, with these arms receiving the chip thermistors. Openings are provided in the upper film to accommodate the thermistors, and the otherwise exposed top surfaces of the thermistors are encapsulated by a conformal coating of polyurethane, or any other suitable fast air drying coating commonly used in printed circuit board applications.

These and other objects will be apparent to one skilled in the art as the following description proceeds in particular reference to the application drawings.

BRIEF DESCRIPTION OF THE DRAWINGS

FIG. 1 is a top plan view showing the sensor assembly of the present invention, with the copper conductors being shown in solid lines for the sake of clarity, FIG. 2 is a fragmentary top plan view of a portion of FIG. 1, showing in more detail the connection of the copper conductors embedded in the sensor assembly to the cable interconnecting the assembly to a monitor or the like, and FIG. 3 is a sectional view taken on line 3—3 of FIG. 1, showing in greatly enlarged form and in more detail the mounting of the chip thermistor to the film layers.

DETAILED DESCRIPTION OF THE PREFERRED EMBODIMENTS

Referring to the application drawing, wherein like parts are indicated by like reference numerals, the sensor assembly of the present invention is generally indicated at 10. The main body of the assembly is comprised of upper and lower layers of film 12 and 14, respectively (FIG. 3) which are secured at their interface by suitable bonding material, for example, an acrylic adhesive which can be either spray coated or in the form of an intervening film to which both the upper and lower films adhere.

The assembly 10 is configured to include enlarged pad portions 16 and 18 at opposite ends of the assembly, and an elongated, relatively narrow main body strip 20. Extending laterally from the main body strip 20 are a lower arm 22 and spaced upper arms 24 and 26, respectively. Thermistors commonly indicated at 30 are positioned near the end of each of the arms as will be described in more detail hereinbelow.

Each thermistor is electrically connected to a copper conductor commonly designated at 32. The thermistors are connected in series and the conductors 32 are preferably enlarged in width in the connecting areas. For example, as can be seen in FIG. 2, each copper conductor 32 is enlarged as shown at 32a to provide a wider contact area for contacts 34 and 36 connected to lead wires commonly indicated at 38 which are encased in cable 40. The cable is connected to a bend relief section 42 which is connected to a plug 44 which can be connected to a monitor or the like. The bend relief section 42 and plug 44 form no part of the present invention and have been shown essentially schematically in FIG. 1.

The copper conductors 32 are provided on the top surface of the lower film 14 preferably by etching. A common method of doing this is to coat the entire top surface of the lower layer 14 with copper, and then to etch away all areas except for areas representing the conducting strips 32. As noted, the non-etched areas are enlarged near the areas connecting the conductors to the thermistors and to the leads 38 of the cable 40.

The chip thermistor 30 is mounted near the outer end of arm 22, and is adapted to be positioned adjacent the mouth of the user, as will be hereinafter described. The thermistor 30 is per se well known in the art, being identified as a surface mount thermistor chip (10K ohms at 25° C.) manufactured by Thermometrics, Edison, N.J. The chip thermistor is approximately 0.1" in length, 0.052" in width, and 0.024" in height, with the opposed upper pads or contact surfaces being slightly elevated above the center connecting portion of the chip.

Referring to FIG. 3, the thermistor pads are positioned generally above the enlarged copper conductor strip portions 32a and are soldered thereto. It should be emphasized that FIG. 3 shows all of the described components in exaggerated dimension, with the copper conductor strip actually being only approximately 0.002" in thickness. Openings 50 are formed in the upper layer 12 above the strip portions 32a and in the vicinity of the thermistor 30, with the film 12 in such areas being raised to extend over the strips. The thermistor 30 rests on the raised surfaces of the film, as illustrated. The thermistor is then soldered to the strips 32a as shown at 51.

In order to electrically isolate the chip thermistors and the adjacent copper conductor at each thermistor connection, an inert thermally conductive conformal coating 52 can be brushed over or sprayed on the connection in order to seal the area, with the coating also extending into the area below the thermistor, as shown. The coating is preferably a fast drying polyurethane coating well suited for general printed circuit board applications, and no invention resides in the coating employed. The thickness of the coating is such that it does not detract from the thermal conductivity of the thermistor.

The chip thermistors mounted in the arms 24 and 26 are mounted in precisely the same fashion as shown in FIG. 3. The arms 24 and 26 are spaced approximately the spacing of the nostrils, and the upper thermistors are, when positioned as described below, spaced from the lower thermistor 30 in arm 22 such that the latter is positioned generally in front of the mouth of the user when the assembly is mounted.

The pads 16 and 18 and the main body strip 20 are formed of a very thin plastic film, for example, approximately 0.002" in thickness. The polyamide film sold under the trademark "Kapton" by DuPont has proved highly satisfactory in use. As above described, the films 12 and 14 can be bonded in any suitable, well-known manner, with the total thickness of the assembly, including the copper conductors but excluding the chip thermistors, being approximately 0.006–0.008", with one exception. The upper film 12 is spaced from the lower film 14 in the area immediately overlying the connection of the cable 40 to the strips 32a at the periphery of the pad 18, as shown at 53 in FIG. 1. This is for the purpose of reducing strain at the connection since the leads are soldered in place before the upper film 12 is adhesively secured to the lower film. It also provides a flat surface on the film 14 opposed to the strain relief area.

The sensor assembly is manufactured as follows. The top surface of the bottom film 14 is provided with a copper layer covering its entire surface, and such layer is etched away as above described to leave the copper conducting strips 32 and their widened ends 32a at the points of connection to the thermistors and cable lead wires. The contacts 34 and 36 of lead wires 38 of cable 40 are then soldered to the adjacent copper sections 32a. The upper film 12, with strain relief area 53, and openings 50 formed therein corresponding to the locations of the thermistors 30, is then adhesively secured to the lower film thereby to provide a laminate comprised of the upper and lower films 12 and 14, the copper conductors 32, and the adhesive. The chip thermistors 30 are then positioned in the openings 50 over the exposed widened portions 32a of the copper conductors at each location and soldered to the copper conductors. A polyurethane coating 52 is then brushed or sprayed over each chip thermistor 30 and the exposed copper conductor.

Spaced lines of unconnected copper, shown in dash lines at 54 in FIG. 1., are left in the arms 24 and 26 during the etching process. These spaced lines 54 define therebetween a fold line which comprises an axis about which the outer ends of the arms 24 and 26 are rotated or folded. The fold lines permit the bending of the arm to overcome the inherent resiliency of the arms.

By providing the fold lines defined by lines 54, the arms can be bent at an angle relative to the flat plane of the assembly so as to be better exposed to normal airflow into and from the nostrils. Once folded, for example, at an angle approaching 90° relative to the flat main body strip, the bent arms will tend to remain in their bent position. This bending of the arms provides for maximum flow of expired air over the thermistors.

Openings commonly designated at 56 extend through both upper and lower layers 12 and 14, on either side of the connecting portions of thermistors 30. The purpose of these openings is to provide airflow to enhance heating or cooling in the area immediately around the thermistors. This allows the thermistors to change state instantaneously so that a more pronounced definition of the breathing cycle can be displayed during visual monitoring. The openings 56 also serve to reduce the mass of the entire assembly.

A thermistor tape (not shown) which is well known and which is used to adhesively secure the assembly to the face of the user can be supplied with the sensor assembly. The tape is preferably a foam tape with a double-sided adhesive layer and release papers applied to each side of the layer. A thermistor tape which has proved satisfactory in use is identified by product number 1511 of the 3M Company, and comprises a double-sided, closed cell, hypo-allergenic PVC foam tape. The bottom release layer is removed and the tape is applied to the pads and the main body strip of the film 12 or 14 of the assembly. The foam tape is very similar in configuration and dimension to those parts of the assembly, but excludes areas corresponding to the arms 22, 24 and 26. Thus, there is no problem of adhering the entire area of the foam tape to the sensor assembly. After the foam tape is adhered to the surface of films 12 or 14, the other release paper can be removed therefrom and the assembly applied to the face of the user. In such application, the arms 24 and 26 are positioned aligned with the nostrils of the user, and in such position the thermistor 30 should be generally aligned with the mouth of the user. It will be understood that the sensor assembly can be provided in various sizes to accommodate use by infants up to mature adults.

The application of the sensor assembly to the face of the user can thus be performed quickly and easily, and with a minimum of discomfort. Due to the relatively thin nature of the final assembly, the assembly is very flexible and can accommodate various curvatures on the face, although the pads 16 and 18 will generally fall into the cheek areas where there is solid backing beneath the skin. Due to its thinness and the manner in which the conducting components are embedded or encapsulated in the assembly, the assembly is very light in weight which further minimizes patient discomfort.

The sensor assembly is normally applied at night when patients are most likely to be unattended. The assembly is normally removed the following morning when the patient is awake. At that time, the foam tape can be removed from the assembly, the mounting surface of the assembly cleaned, and a new foam tape applied. Since the foam tape is the only portion of the assembly actually contacting the skin of the patient, the assembly can be repeatedly re-used, with little or no deterioration, even assuming regular sterilization.

It will thus be seen that the objectives of the invention have been accomplished. The sensor assembly, with the embedded copper strips and encapsulated chip thermistors, is very thin and flexible, and can be easily configured to the curvature of the user in the area of the cheeks. A separate double-sided foam tape is applied to one side of the assembly to be mounted on the user, with the foam tape serving to firmly retain the sensor assembly in its aligned position. It does not matter which film surface the tape is applied to insofar as thermistor operation is concerned. However, the surface of film 14 is normally preferred since the strain relief 53 extends outwardly for the surface 12 and impairs the degree of facial contact with the assembly in that area, in addition to increasing discomfort.

Expired air passes over the chip thermistors 30 mounted in the arms 22, 24, and 26, respectively, with the resistance of the thermistors varying accordingly, and providing a signal which can be monitored in a well-known manner. The assembly is comparatively inexpensive to manufacture and is highly durable in use. All components are either embedded or encapsulated whereby replacement of the foam tape and minor cleaning of the adhering surface is all that is necessary for re-use of the assembly. This even further reduces costs on a per use basis.

Modifications of the invention described will suggest themselves to those skilled in the art. For example, rather than provide separate spaced arms for detecting nasal airflow, a single arm with spaced thermistors could be provided. Where the sensor assembly is for infant use, a single arm and single thermistor chip can be utilized in view of the substantially smaller dimensions.

Rather than mounting the thermistor chips in openings in the upper film and applying conformed coatings to electrically isolate the thermistor and circuit, the upper film, if sufficiently pliable, could perform that function. This would eliminate the extra step of coating.

What is claimed is:

1. A thermistor airflow sensor assembly adapted to be mounted adjacent the mouth and nose of a patient for monitoring the breathing of such patient, comprising:

a) upper and lower layers of thin, flexible, resilient plastic film readily conformable to the facial curvatures of the patient, said layers being essentially identical in shape and configured to include an elongated main body strip, longitudinal end portions serving as primary mounting pads for the assembly, a first leg extending laterally form said main body strip and having an outer end adapted to be generally aligned with the mouth of the patient when the assembly is mounted, and a pair of longitudinally spaced legs having outer ends and extending laterally form said main body strip in a direction opposed to said first leg, the outer end of each of said pair of legs being aligned with the nostrils of the patient when the assembly is mounted;

b) said layers being laminated to each other over substantially their entire surfaces, c) circuit conductors between said layers, said conductors extending to said outer ends of each of said legs and to a periphery of one of said end portions, and being adapted to be electrically connected to a monitor;

d) the outer ends of said legs of said upper layer being formed with openings below which said circuit conductors extend and are exposed;

e) thermistor means for sensing air temperature mounted in each of said openings and electrically connected to said circuit conductors, said thermistor means projecting outwardly from a surface of the upper film layer to provide exposed surfaces over which exposed air form the patient's mouth and nose can pass;

f) an electrically insulative coating over the exposed surfaces of said thermistor means for electrically isolating said thermistor means and said circuit conductors from said patient, whereby said thermistor means detects the temperature of ambient and expired air and transmits signals through said circuit conductors indicative of such temperatures.

2. The sensor assembly of claim 1, wherein said circuit conductors comprise copper conductors in the form of copper strips adhered to an inner surface of said lower film, said copper strips extending to areas below the openings in said upper film in which said thermistor means are positioned, said thermistor means being soldered to said copper strips.

3. The sensor assembly of claim 2, wherein said thermistor means comprise chip thermistors including thermistor pads positioned over said copper strips and soldered thereto.

4. The sensor assembly of claim 2, wherein said copper strips extend generally diametrically through one of said longitudinal end portions, said sensor assembly further including a cable having connectors electrically connected to said copper strips, and wherein said upper film in the region of such connection is spaced form said lower film to form a strain relief area to minimize strain on the connection of said circuit to said cable.

5. The sensor assembly of claim 1, wherein openings are formed above and below said thermistor means extending entirely through said upper and lower film layers, said openings permitting air flow over said thermistor means so as to enhance the return of said thermistor means to ambient temperature between expiration cycles.

6. The sensor assembly of claim 1, wherein each of said upper and lower layers of film comprise polyamide film approximately 0.002" in thickness, said layers being adhesively secured to each other thereby embedding said circuit conductor means, the total thickness of said laminate including said circuit conductor means being approximately 0.006"-0.008", except for the location of said thermistor means and the periphery of said one end portion.

7. The sensor assembly of claim 1, further including a thermistor tape adapted to be mounted on one of said film layers, said tape having a bottom release layer the removal of which permits the thermistor tape to be adhesively secured to said one layer, and a top release layer the removal of which permits the sensor assembly to be adhesively secured to the face of the patient, said thermistor tape being configured similarly to said one layer of film except for the omission of said first leg and said pair of spaced legs, whereby said thermistor tape does not overlie said thermistor means and thereby interfere with the mounting of said sensor assembly.

8. The sensor assembly of claim 1 wherein said first leg adapted to be aligned with the mouth of the patient is positioned generally centrally longitudinally of said upper and lower layers of film, and said pair of spaced legs extending in a direction opposite to said first leg are positioned longitudinally to either side of said first leg, whereby said assembly is symmetrical when said pair of legs are aligned with the nostrils of the patient.

9. The sensor assembly of claim 8, wherein fold lines are provided in each of said pair of longitudinally spaced legs between said thermistor means and the main body strip, each of said pair of legs being foldable about said fold lines to move said legs from a position coplanar with said main body strip to a position approaching perpendicularity with respect thereto, whereby said thermistor means associated with each of said legs is more directly exposed to the air expired through the nostrils of the patient.

10. The sensor assembly of claim 9, wherein said fold lines are provided by spaced strips of copper generally perpendicular to said circuit conductors, said spaced copper lines defining therebetween a pivot axis about which said legs can rotate relative to the plane of said main body strip.

* * * * *